United States Patent [19]
Ushijima et al.

[11] Patent Number: 6,099,833
[45] Date of Patent: Aug. 8, 2000

[54] **METHOD FOR INHIBITING PRODUCTION OF TOXINS FROM ENTEROPATHOGENIC *ESCHERICHIA COLI*, AND BUTYRIC-ACID BACTERIA AND BUTYRIC-ACID BACTERIA CONTAINING PHARMACEUTICALS USED IN COMBINATION WITH ANTIBIOTICS FOR THE METHOD**

[75] Inventors: Tsutomu Ushijima, Otsu; Yuiko Matsubara, Mukou, both of Japan

[73] Assignee: Nitto Pharmaceutical Industries Ltd., Kyoto, Japan

[21] Appl. No.: 09/105,915

[22] Filed: Jun. 26, 1998

[30] Foreign Application Priority Data

Jul. 1, 1997 [JP] Japan ................................. 9-175868

[51] Int. Cl.$^7$ ................................. C12N 1/20
[52] U.S. Cl. ................................. 424/93.41
[58] Field of Search ................................. 424/93.41

[56] References Cited

PUBLICATIONS

Tsuyoshi Ushijima, "Semisynthetic Media for In Vitro Examination of the Contributions of Nutrients and Growth Inhibitors for Symbiosis or Antagonism of the Bacteria in Ileum, Caecum and Colon of the Mammalian", *Medical and Biology*, 106, No. 4, 199–204 (1983).

Takashi Shimoyama et al., "Intestinal Bacterial Flora and Disease: Mainly on Large Intestine Disease", *Most Up–to–Date Medical*, 33(10), 2047–2055 (1978).

Tsuyoshi Ushijima, "A Simple Anaerobic Continuous Culture System for the Study of Bacterial Symbiosis and Antagonism", *Medical and Biology*, 108, No. 2, 71–74 (1984).

T. Ushijima and A. Seto, Selected Faecal Bacteria and Nutrients Essential for Antagonism of *Salmonella typhimurium* in Anaerobic Continuous Flow cultures, *J. Med. Microbiol.*, 35, 111–117 (1983).

Tsuyoshi Ushijima, "Difference of Antagonistic Effects of Resident Colonic Bacteria for Enterohemorrhagic *Escherichia Coli* in AnaerobicContinuous Flow Cultures Using Mimic Media of Colonic Contents of Adult and Breast–fed New Born", *Medical and Biology*, 134, No. 5, 149–154 (1997).

Tsuyoshi Ushijima, "Potent Growth Inhibition of Enterohemorragic *Escherichia coli* Some Other Gram Negative Enteropathogens by Resident *Escherichia coli* Grew maximum Level in Anaerobic Cultures", *Medical and Biology*, 134, No. 2, 39–44 (1997).

Tsuyoshi Ushijima, "Potent Antagonistic Effect of Resident *Escherichia coli* in Human Colon on Enteropathogenic and Enterohemorragic *Escherichia coli*", *Medical and Biology*, 127, No. 1, 5–9 (1993).

Tsuyoshi Ushijima, "Antagonistic Effects of Human Colonic Bacteria on Some Enteropathogenic *Escherichia coli*", *Medical and Biology*, 126, No. 1, 9–14 (1993).

*Primary Examiner*—Jean C. Witz
*Attorney, Agent, or Firm*—Frishauf, Holtz, Goodman, Langer & Chick, P.C.

[57] ABSTRACT

A method of treating a human infected with enteropathogenic *Escherichia coli* which produces toxins, by administering to the human a butyric-acid bacteria and an antibiotic, such as fosfomycin.

10 Claims, 4 Drawing Sheets

Fig. 3

METHOD FOR INHIBITING PRODUCTION OF TOXINS FROM ENTEROPATHOGENIC *ESCHERICHIA COLI*, AND BUTYRIC-ACID BACTERIA AND BUTYRIC-ACID BACTERIA CONTAINING PHARMACEUTICALS USED IN COMBINATION WITH ANTIBIOTICS FOR THE METHOD

BACKGROUND OF THE INVENTION

1. Field of the Invention

The present invention relates to a method for inhibiting production of toxins from enteropathogenic *Escherichia coli* and butyric-acid bacteria used for the method. More particularly, the present invention relates to a method for inhibiting production of Vero toxins from EHEC SU 5053 (O157), a method for safely sterilizing enteropathogenic *Escherichia coli* and butyric-acid bacteria and butyric-acid bacteria containing pharmaceuticals to be used for the method.

2. Background Information

To administer an antibiotic to an individual who is infected with enteropathogenic *Escherichia coli* has been known hitherto as a method for sterilizing the enteropathogenic *Escherichia coli*.

Of the enteropathogenic *Escherichia coli*, some bacteria, e.g., EHEC SU 5053 (O157) can cause toxins produced in cells to be liberated when cells become extinct or when the number of toxins reach the permissible maximum. Among of others, some toxins are so dangerous that they can cause not only hemorrhagic diarrhea, but also hemolytic uremic syndrome, to destroy cell membranes, such as red blood cells, which may lead to death of an individual. To administer an antibiotic to an individual who is infected with such dangerous bacteria induces toxins to be liberated when the bacteria becomes extinct due to the antibiotic, and further the toxins liberated are accumulated in the body (particularly in the intestinal tract). For this reason, it is significantly dangerous to administer an antibiotic to an individual infected with such dangerous bacteria. Also, if the number of toxins have already reached the permissible maximum before the antibiotic is administered, the toxins are already in liberation, and accordingly it is further significantly dangerous to administer the antibiotic to such an individual infected with the bacteria in that condition.

It is known, on the other hand, that multiplication of EHEC SU 5053 (O157) is strongly inhibited by mixed culture of human intestine indigenous *Escherichia coli* with EHEC SU 5053 (O157) of a kind of enteropathogenic *Escherichia coli* (Cf. USHIJIMA, Tsuyoshi, "Difference in antagonism effects of resident clonic bacteria for enterohemorrhagic *Escherichia coli* in anaerobic continuous cultures mimic media of adult and breast-fed newborn", *Medical and Biology*, 134(5):149–154, 1997; USHIJIMA, Tsuyoshi, "Potent growth inhibition of enterohemorrhagic *Escherichia coli* and some other gram negative *Escherichia coli* endopatnogens by resident grew maximum level in anaerobic cultures", *Medical and Biology*, 134(2):39–44, 1997; USHIJIMA, Tsuyoshi, "Potent antagonism effect of resident *Escherichia coli* in human colon on enteropathogenic enterohemorrhagic *Escherichia coli* and", Medical and Biology 127(1):5–9, 1993; and USHIJIMA, Tsuyoshi, "Antagonism effects of human colonic bacteria on some entergathogenic *Escherichia coli*", *Medical and Biology*, 126(1):9–14, 1993).

However, if fosfomycin (a cell wall synthetic inhibitor), which is an antibiotic, is added to the culture solution, then a large amount of Vero toxins will be liberated in the culture solution when EHEC SU 5053 (O157) becomes extinct. This indicates that human intestine indigenous *Escherichia coli* serves to inhibit toxins produced in the enteropathogenic *Escherichia coli* EHEC SU 5053 (O157) from being liberated in the culture solution in the process of multiplication of the enteropathogenic *Escherichia coli* EHEC SU 5053 (O157), but will not serve to inhibit toxins produced in the enteropathogenic *Escherichia coli* from being liberated in the culture solution, if fosfomycin is added thereto.

Accordingly, there has been being desired a method for inhibiting bacteria, which can produce toxins when cells becomes extinct (e.g., EHEC SU 5053 (O157)), from producing toxins in an individual who is infected with such bacteria and further administering antibiotic to the individual safely, to sterilize the bacteria safely, and a pharmaceutical used for the method.

The present inventors have discovered that enteropathogenic *Escherichia coli* is considerably inhibited from producing toxins (Vero toxins, in particular) by inoculating butyric-acid bacteria into an area contaminated by the enteropathogenic *Escherichia coli* and in turn adding an antibiotic thereto. They also have discovered that enteropathogenic *Escherichia coli* is considerably inhibited from producing toxins and is safely sterilized also by inoculating butyric-acid bacteria into an area having human intestine indigenous *Escherichia coli* (hereinafter it is sometimes referred to as "human intestine indigenous *E. coli*") and contaminated by the enteropathogenic *Escherichia coli* and in turn adding an antibiotic thereto. Based on these discoveries, the present inventors have accomplished the present invention.

SUMMARY OF THE INVENTION

The present invention is directed to a novel method for inhibiting production of toxins from enteropathogenic *Escherichia coli* significantly in an area contaminated by the enteropathogenic *Escherichia coli*, a method for safely sterilizing the enteropathogenic *Escherichia coli* by use of the method, and butyric-acid bacteria and a butyric-acid bacteria containing a pharmaceutical to be used for the method.

To solve the aforesaid problems, a method according to the invention for inhibiting production of toxins from enteropathogenic *Escherichia coli* comprises the step of adding butyric-acid bacteria and an antibiotic to an area contaminated by the enteropathogenic *Escherichia coli*.

Preferably, the area contaminated by the enteropathogenic *Escherichia coli* has human intestine indigenous *Escherichia coli*, from the point of view that *Clostridium butyricum* FERM P-14285, when coexisting with human intestine indigenous *Escherichia coli* in the area, promotes inhibition of the production of toxins from enteropathogenic *Escherichia coli*. Human intestine indigenous *Escherichia coli* may be added to the area contaminated by the enteropathogenic *Escherichia coli*. The human intestine indigenous *Escherichia coli* which may be used includes *E. coli* ATCC 25922, for example.

A method for safely sterilizing enteropathogenic *Escherichia coli* that liberates toxins comprises the step of adding butyric-acid bacteria and an antibiotic to an area contaminated by enteropathogenic *Escherichia coli* which can produce toxins and having human intestine indigenous *Escherichia coli*. The human intestine indigenous *Escherichia coli* is the same as that previously described.

It is noted here that the term "production of toxins" used in this specification is intended to include not only the state in which toxins are produced, but also the state in which the produced toxins are liberated and accumulated.

As for the butyric-acid bacteria, any butyric-acid bacteria may be used, as long as they are of the butyricum species of a Clostridium group. The butyric-acid bacteria which may be used include *Clostridium butyricum* FERM P-14285, for example.

It is noted that the *Clostridium butyricum* FERM P-14285 (FERM BP-6393) is the butyric-acid bacteria which was deposited as *Clostridium butyricum* NT on Apr. 21, 1994 in the Biotechnology Industrial Technology Institute of Industrial Technology Authority of Japan. (The National Institute of Bioscience and Human Technology, Agency of Industrial Science and Technology, at 1–3 Higashi 1 chome, Tsukuba-shi, Ibaraki-ken, Japan)

The enteropathogenic *Escherichia coli* include enterohemorrhagic *Escherichia coli* (EHEC), for example. The method of the invention is particularly effective for Vero toxins (Vero toxin type I and Vero toxin type II) produced by EHEC SU 5053 (O157), in particular, of the toxins produced by the enterohemorrhagic *Escherichia coli* (EHEC).

As for the antibiotics, any selected antibiotics which enable the Vero toxins to be inhibited by the interaction with butyric-acid bacteria may be used. The antibiotic used should properly be selected in accordance with a condition of a patient infected with enteropathogenic *Escherichia coli*. The antibiotics which may be used include a cell wall synthetic inhibitor, for example, and fosfomycin and the metallic salts thereof are preferable. The metallic salts of fosfomycin include the sodium salt, the di-sodium salt and the calcium salt, for example.

The areas contaminated by enteropathogenic *Escherichia coli* include, for example, culture solution containing EHEC SU 5053 (O157) and an intestinal tract of a patient infected with EHEC SU 5053 (O157), though no particular restriction is imposed on the area.

On the other hand, the butyric-acid bacteria of the type according to the invention are so formed as to be used in combination with an antibiotic, to inhibit production of toxins from the enteropathogenic *Escherichia coli*. The butyric-acid bacteria used in combination with the antibiotic could inhibit production of toxins from enteropathogenic *Escherichia coli*, as will be described later in the embodiments of the invention. The butyric-acid bacteria enable the enteropathogenic *Escherichia coli* to be safely sterilized by their combined use with a human intestine indigenous *Escherichia coli* and an antibiotic.

It is noted that the butyric-acid bacteria, the human intestine indigenous *Escherichia coli*, the enteropathogenic *Escherichia coli*, the toxins from the enteropathogenic *Escherichia coli*, the areas contaminated by enteropathogenic *Escherichia coli*, and the antibiotics are the same as the previously described ones.

The form of butyric-acid bacteria containing pharmaceuticals containing the butyric-acid bacteria of the type according to the invention should preferably be in the form of a powder, from the viewpoint of handling, although such is not restrictive. The butyric-acid bacteria containing pharmaceuticals containing the butyric-acid bacteria of this type according to the invention also falls within the scope of the present invention.

The butyric-acid bacteria containing pharmaceuticals containing the butyric-acid bacteria of the type according to the invention may contain an additive, as required, unless it exerts a harmful influence on the inhibition of the production of Vero toxins. The additives which may be used include diluents, lubricants, disintegrants, preservatives, dissolution adjuvants, disintegration extenders, emulsifying agents, suspending agents, and suppository bases. The diluents which may be used to the butyric-acid bacteria containing pharmaceuticals of the type according to the invention include dry potato starch, for example.

BRIEF DESCRIPTION OF THE DRAWINGS

The invention will now be described with reference to the accompanying drawings wherein.

DETAILED DESCRIPTION OF THE PREFERRED EMBODIMENT OF THE INVENTION

The method according to the invention for inhibiting the production of toxins from enteropathogenic *Escherichia coli* and the method according to the invention for sterilizing the enteropathogenic *Escherichia coli* each comprise the step of adding *Clostridium butyricum* FERM P-14285 as butyric-acid bacteria and in turn adding fosfomycin as an antibiotic to the culture solution containing enteropathogenic *Escherichia coli* EHEC SU 5053 (O157) as an enterohemorrhagic *Escherichia coli* and *E. coli* ATC 25922 as the human intestine indigenous *Escherichia coli*. It is well known that the enteropathogenic *Escherichia coli* EHEC SU 5053 (O157) produces the Vero toxins (Vero toxin type I and Vero toxin type II).

The method according to the invention for inhibiting the production of toxins from enteropathogenic *Escherichia coli* and the method according to the invention for sterilizing the enteropathogenic *Escherichia coli*, each including the above-described step, can produce the following effects.

Addition of *Clostridium butyricum* FERM P-14285 and fosfomycin to the culture solution containing human intestine indigenous *Escherichia coli* of *E. coli* ATC 25922 and enteropathogenic *Escherichia coli* of EHEC SU 5053 (O157) enables the production of Vero toxins from the enteropathogenic *Escherichia coli* of EHEC SU 5053 (O157) to be considerably inhibited by the interaction therebetween and sequentially enables the enteropathogenic *Escherichia coli* of EHEC SU 5053 (O157) to be safely sterilized by the fosfomycin.

When the culture solution containing the enteropathogenic *Escherichia coli* of EHEC SU 5053 (O157) contains human intestine indigenous *Escherichia coli* of *E. coli* ATC 25922, the multiplication of EHEC SU 5053 (O157) is inhibited and the liberation of Vero toxins into the culture solution in the process of multiplication of bacteria is also inhibited. This is known by the four publications cited in the Background Information section of this application. However, attempts to sterilize the enteropathogenic *Escherichia coli* of EHEC SU 5053 (O157) by use of fosfomycin for example will then cause Vero toxins to be liberated into the culture solution.

According to the method of the present invention, the production of Vero toxins in the culture solution containing the enteropathogenic *Escherichia coli* of EHEC SU 5053 (O157) and the human intestine indigenous *Escherichia coli* of *E. coli* ATCC 25922 is inhibited not only by the human intestine indigenous *Escherichia coli* of *E. coli* ATCC 25922 but also by *Clostridium butyricum* FERM P-14285. Particularly in the case of fosfomycin being added thereto, the production of Vero toxins are further significantly inhibited by the interaction thereamong.

Fosfomycin is a cell wall synthetic inhibitor and accordingly it enables the enteropathogenic *Escherichia coli* of EHEC SU 5053 (O157) to be sterilized. By the interaction among the three as described above, the production of Vero toxins is inhibited, while the enteropathogenic *Escherichia coli* of EHEC SU 5053 (O157) is safely sterilized.

Thus, the production of Vero toxins are inhibited by the interaction among the human intestine indigenous *Escherichia coli* of *E. coli* ATCC 25922, the *Clostridium butyricum* FERM P-14285 and the fosfomycin, and as such can allow the production of Vero toxins to be further significantly inhibited, with the EHEC SU 5053 being safely sterilized. Hence, fosfomycin can be very safely administered to a patient infected with the enteropathogenic *Escherichia coli*.

It is known that the bacteria level of human intestine indigenous *Escherichia coli* increases when an individual suffers from diarrhea (Cf. e.g., Takashi SHIMOYAMA et. al., "Intestinal bacterial flora and Disease: Mainly on large intestine disease", Most Up-to-date Medical 33(10):2047–2055, 1978). Usually, contamination by the enteropathogenic *Escherlchia coli* of EHEC (O157) causes the bacteria level of human intestine indigenous *Escherichia coli* of *E. coli* to increase in the intestinal tract in a state of diarrhea, for the reason of which the inhibition of production of Vero toxins by *Clostridium butyricum* FERM P-14285 and fosfomycin is further significantly promoted. Thus, the method of the invention is most effective for an individual in a state of diarrhea whose intestinal tract is contaminated by the enteropathogenic *Escherichia coli* of EHEC (O157).

In comparison with the known enteropathogenic *Escherichia coli* sterilizing method in which only the fosfomycin is singly added to an area contaminated by the enteropathogenic *Escherichia coli* EHEC (O157) that can produce Vero toxins, the method of the invention can provide the results that the multiplication of EHEC SU 5053 (O157) is inhibited by the human intestine indigenous *E. coli* and that not only the EHEC (O157) is sterilized by fosfomycin but also the production of Vero toxins by the EHEC (O157) is prevented by the interaction between the fosfomycin and *Clostridium butyricum* FERM P-14285 or by the interaction among the human intestine indigenous *E. coli*, the fosfomycin and the *Clostridium butyricum* FERM P-14285. Resultantly, the development of hemolytic uremic syndrome that could result in death is inhibited while the multiplication of EHEC (O157) is prevented, and further the enteropathogenic *Escherichia coli* EHEC (O157) is sterilized. The contents above will be detailed in Example 1 as will be described later.

MODIFIED EMBODIMENT 1

A modified method according to the invention for inhibiting the production of toxins from enteropathogenic *Escherichia coli* comprises the step of adding *Clostridium butyricum* FERM P-14285 as a butyric-acid bacteria and in turn adding fosfomycin as an antibiotic to the culture solution containing enteropathogenic *Escherichia coli* EHEC SU 5053 (O157) which is a kind of an enterohemorrhagic *Escherichia coli*.

The modified method comprising the above-described step for inhibiting the production of toxins from enteropathogenic *Escherichia coli* can produce the following effect.

Addition of *Clostridium butyricum* FERM P-14285 and fosfomycin to the culture solution containing enteropathogenic *Escherichia coli* EHEC (O157) can cause the production of Vero toxins from the enteropathogenic *Escherichia coli* EHEC (O157) to be inhibited by the interaction therebetween. The contents above will be detailed in Example 2 as will be described later.

MODIFIED EMBODIMENT 2

On the other hand, the butyric-acid bacteria according to the invention, when used in combination with an antibiotic, contributes to inhibition of the production of toxins from enteropathogenic *Escherichia coli*. The butyric-acid bacteria which may be used include *Clostridium butyricum* FERM P-14285, for example.

In use, the butyric-acid bacteria above is combined with fosfomycin (a cell wall synthetic inhibitor) as an antibiotic, and is administered to a patient who is infected with the enteropathogenic *Escherichia coli* EHEC (O157) and also is ill with diseases caused by the Vero toxins. The butyric-acid bacteria containing pharmaceuticals thus administered are combined with the fosfomycin, and thereby the interaction is produced therebetween, as is the case with the above, to cause the production of Vero toxins to be significantly inhibited. By virtue of this, in a patient infected with the enteropathogenic *Escherichia coli* EHEC (O157), the development of hemolytic uremic syndrome is inhibited while the multiplication of EHEC (O157) is prevented, and the enteropathogenic *Escherichia coli* EHEC (O157) is safely sterilized. These butyric-acid bacteria can be combined with proper diluents, to be manufactured and sold as the butyric-acid bacteria containing pharmaceuticals. These butyric-acid bacteria containing pharmaceuticals are used mainly for medical drugs.

EXAMPLES

While the invention will be described in more detail with reference to the following Examples, it is to be understood that the following Examples are for the purpose of illustration and not of limitation.

Composition of Culture Solution

The culture solution employed in the Example contains the following components per 100 ml of distilled water.

| | |
|---|---|
| Soluble starch | 0.2 g |
| Glucose | 0.05 g |
| Lactose | 0.1 g |
| Sorbose | 0.05 g |
| $(NH_4)_2SO_4$ | 0.2 g |
| $KH_2PO_4$ | 0.7 g |
| $Na_2HPO_4$ | 1 g |
| $Na_2CO_3$ (anhydrous) | 0.1 g |
| NaCl | 0.2 g |
| $MgSO_4 \cdot 7H_2O$ | 0.01 g |
| CaCl2 | 0.001 g |
| $FeSO_4 \cdot 7H_2O$ | 0.0005 g |
| Yeast Extract | 0.01 g |
| L-cysteine hydrochloride 1 hydrate | 0.02 g |
| Sodium Thioglycolate | 0.02 g |
| Powdered Bile | 0.005 g |
| Sodium palmitate | 0.005 g |
| Sodium stearate | 0.005 g |
| Sodium linoleate | 0.002 g |
| Sodium oleate | 0.002 g |
| Tween 80 (Trade name) | 0.025 g |
| Hemin | 0.001 g |
| Vitamin $B_{12}$ | 0.00005 g |

-continued

| | |
|---|---|
| Vitamin K₃ | 0.00001 g |
| Anti-foaming agent (1) | 0.01 g |
| Amino acid (2) | 5 μmol |

(1): "TORAY SILICONE" (Trade name, available from TORAY SILICONE CO. LTD.)
(2): The amino acid contains 17 kinds of amino acids selected from 20 kinds of major L-Amino acids forming proteins, except Cysteine, Cystine and oxyproline (Asparagine, Threonine, Serine, Glutamine, Proline, Glycine, Alanine, Valine, Methionine, Isoleucine, Leucine, Tyrosine, Phenylalanine, Lysine, Histidine, Arginine and Tryptophan).

A detailed description on the composition of the above-described culture medium is given by USHIJIMA, Tsuyoshi, "semisynthetic media for vitro examinations of the contributions of nutrients and growth inhibitors for symbiosis or antagonism of the bacteria inileum caeuim and of the mammalian", *Medical and Biology*, 106(4): 199–204, 1983.

See the above-described culture solution and simplified anaerobic continuous culture apparatus (USHIJIMA Tsuyoshi, "A simple araerobic continuous culture system for the study of bacterial symbiosis and antagonism of" *Medical and Biology*, 108(2): 71–74, 1984 and Ushijima, T. and Seto, A.: "Selected faecal bacteria and nutrients essential for antagonism of Salmonella typhimurium in anaerobic continuous flow cultures", *J. Med. Microbiol.*, 35:111–117, 1991), which are disclosed by these publications and are used to perform the following experiments.

Vero Toxins Detecting Kit

The Vero toxins detecting kit used in the following Examples is an *Escherichia coli* Vero toxins detecting kit ("VTEC-RPLA (SEIKEN)") (hereinafter it is simply referred to as "the kit") available from DENNKA SEIKEN CO., LTD.

The kit includes the following latexes, control Vero toxins, and diluting solution:

(1) Sensitization Latex VT1

This sensitization latex VT1 contains a specific antibody (Rabbit IgG) of Vero toxins type I and sodium azide (0.1%) as a preservative.

(2) Sensitization Latex VT2

This sensitization latex VT2 contains a specific antibody (Rabbit IgG) of Vero toxins type II and sodium azide (0.1%) as a preservative.

(3) Control Latex

This control latex contains a normal Rabbit IgG and sodium azide (0.1%) as a preservative.

(4) Control Vero Toxins Type I

This control Vero toxins type I contains Vero toxins type I in a freeze-drying condition, lactose as a preservative, and bovine serum albumin.

(5) Control Vero Toxins Type II

This control Vero toxins type II contains Vero toxins type II in a freeze-drying condition, lactose as a preservative, and bovine serum albumin.

(6) Diluting Solution

This diluting solution is phosphatic buffer sodium chloride solution (PBS) containing bovine serum albumin (0.5%) and sodium azide (0.1%) as a preservative.

Method for Preparing *E. coli* ATCC 25922 Containing Solution *E. coli* ATCC 25922 was inoculated into semisolid stock culture medium (pH of about 7.0) containing the following components and then was incubated overnight, to prepare *E. coli* ATCC 25992 containing culture medium. The resultant culture medium was added to sterilized physiological saline solution (about 2 ml), to prepare *E. coli* ATCC 25992 containing solution. Then, the *E. coli* ATCC 25992 containing solution was measured in respect of the number of bacteria via a tenfold stepwise dilution, the result being about $10^8$cfu/ml (McFarland No. 3–4, a slightly clouded level).

The above-described semisolid stock culture medium contains the following components per 100ml distilled water.

| | |
|---|---|
| Trypticase peptone (BBL) | 1 g |
| Proteose peptone No. 3 (Difco) | 0.5 g |
| Meat extract (available from Kyokuto Pharmaceuticals Co., Ltd.) | 0.3 g |
| Yeast extract (BBL) | 0.2 g |
| Glucose | 0.3 g |
| Soluble starch | 0.1 g |
| NaCl | 0.5 g |
| Na₂CO₃ (anhydrous) | 0.1 g |
| KH₂PO₄ | 0.4 g |
| L-cysteine hydrochloride 1 hydrate | 0.02 g |
| Sodium Thioglycolate | 0.02 g |
| Agar | 0.15 g |
| Tween 80 (Trade name) | 0.03 g |
| Hemin | 0.001 g |
| Vitamin K3 | 0.00001 g |

Method for Preparing EHEC SU 5053 Containing Solution

EHEC SU 5053 was inoculated into semisolid stock culture medium (pH about 7.0) containing the same components as those in the above and then was incubated overnight, to prepare the EHEC SU 5053 containing culture medium. The resultant culture medium was added to sterilized physiological saline solution (about 2 ml), to prepare EHEC SU 5053 containing solution. Then, the EHEC SU 5053 containing solution was measured in respect of the number of bacteria via the tenfold stepwise dilution, the result being about $10^8$cfu/ml (McFarland No. 3–4, a slightly clouded level).

Method for Preparing *Clostridium butyricum* FERM P-14285 Containing Solution

*Clostridium butyricum* FERM P-14285 was inoculated into semisolid stock culture medium (pH of about 6.8) containing the following components and then was incubated overnight, to prepare *Clostridium butyricum* FERM P-14285 containing culture medium. The resultant culture medium was added to sterilized physiological saline solution (about 2 ml), to prepare *Clostridium butyricum* FERM P-14285 containing solution. Then, the *Clostridium butyricum* FERM P-14285 containing solution was measured in respect of the number of bacteria via the tenfold stepwise dilution, the result being about $10^8$cfu/ml (McFarland No. 3–4, a slightly clouded level).

The above-described semisolid stock culture medium contains the following components per 100 ml distilled water.

| | |
|---|---|
| Trypticase peptone (BBL) | 1 g |
| Proteose peptone No. 3 (Difco) | 0.5 g |
| Yeast extract (BBL) | 0.02 g |

-continued

| | |
|---|---|
| Lactose | 0.3 g |
| Na$_2$HPO$_4$ | 0.5 g |
| KH$_2$PO$_4$ | 0.5 g |
| NaCl | 0.3 g |
| MgSO$_4$.H$_2$O | 0.01 g |
| L-cysteine hydrochloride 1 hydrate | 0.02 g |
| Tween 80 (Trade name) | 0.03 g |
| Agar | 0.05 g |

Example 1

The above-described culture solution (about 130 ml) of about 37° C. was filled in a culture incubator. Then, in order to reproduce the environment of the diarrhetic intestine under which the bacteria of an aerobic bacteria group increases in number and the bacteria of an anaerobic bacteria group decreases in number, the *E. coli* ATCC 25922 containing solution, *Clostridium butyricum* FERM P-14285 containing solution, and EHEC SU 5053 containing solution as described above were inoculated into the culture solution to cause the number of bacteria in each of the solution to be about 10$^6$cfu/ml.

Then, the culture continued at about 37° C. for about 24 hours, while an about 5 W/W % (about 6.5 ml) of culture solution was removed from the culture solution (about 130 ml) in the culture incubator once every hour but instead the same amount of fresh culture medium was added (hereinafter this operation is called as "the culture medium flow rate of 5%/hr."). At this point in time, the number of bacteria in each of the *E. coli* ATCC 25922, the *Clostridium butyricum* FERM P-14285 and the EHEC SU 5053 was measured via the respective selective medium shown below.

In detail, the number of bacteria was measured in the following manner. First, the culture solution (0.1 ml) was taken out of each of the culture incubator and was diluted tenfold stepwise with sterilized physiological saline solution. Then, the respective diluted solution as diluted tenfold stepwise (0.1 ml, 10$^1$–10$^{10}$-fold dilution) was applied to the respective selective medium, which in turn was cultured at about 37° C. for about 48 hours. From the selective mediums, the culture mediums in which the number of bacteria could be measured (the culture mediums in which about 30 to 100 colonies were generated) were selected, and the number of colonies was measured with a visual inspection and then the respective number of bacteria in the culture solution was calculated.

The selective medium for *E. coli* ATCC 25922 contains the following components per 100 ml distilled water.

| | |
|---|---|
| NaCl | 0.5 g |
| NaH$_2$PO$_4$ | 0.4 g |
| Na$_2$CO$_3$ (anhydrous) | 0.1 g |
| (NH$_4$)$_2$SO$_4$ | 0.2 g |
| MgSO$_4$.7H$_2$O | 0.01 g |
| Sorbose | 0.5 g |
| Sodium thiosulfate (anhydrous) | 0.1 g |
| Agar | 1.5 g |
| Yeast extract | 0.005 g |
| Sodium deoxycholate | 0.02 g |
| Sodium linoleate | 0.02 g |

-continued

| | |
|---|---|
| Neutral red | 0.002 g |
| Van Gieson (Amphotericin B) | 0.0005 g |

The above components except Van Gieson were heated to be dissolved and thereafter were cooled down to about 55° C., and then the Van Gieson was added to the resultant and mixed to form a plate culture medium (pH of about 7).

When *E. coli* ATCC 25922 is inoculated into the plate culture medium and then incubated for about 48 hours, a large red colony of *E. coli* ATCC 25922 is detected. In this culture medium, EHEC is detected in the form of a small light pink colony.

The selective medium for *Clostridium butyricum* FERM P-14285 contains the following components per 100 ml distilled water.

| | |
|---|---|
| Trypticase peptone (BBL) | 1 g |
| Proteose peptone No. 3 (Difco) | 0.5 g |
| Yeast extract (BBL) | 0.1 g |
| Lactose | 0.5 g |
| KH$_2$PO$_4$ | 1.0 g |
| NaCl | 0.5 g |
| L-cysteine hydrochloride 1 hydrate | 0.02 g |
| Sodium acetate | 0.5 g |
| Agar | 1.5 g |
| Tween 80 (Trade name) | 0.03 g |
| Amphotericin B | 0.0005 g |
| Trimethoprim | 0.003 g |
| Kanamycin | 0.005 g |
| Polymyxin B | 10$^4$ units |
| Penicillin G | 10$^3$ units |
| Methyl Red | 0.001 g |

The above components except Amphotericin B, Trimethoprim, Kanamycin, Polymyxin B and Penicillin G were heated to be dissolved and thereafter were cooled down to about 50° C. to about 55° C., and then Amphotericin B, Trimethoprim, Kanamycin, Polymyxin B, and Penicillin G were added to the resultant composition and mixed to form a plate culture medium (pH of about 5.5).

When *Clostridium butyricum* FERM P-14285 is inoculated into this plate culture medium and then incubated at about 37° C. for about 48 hours to about 72 hours, the *Clostridium butyricum* FERM P-14285 is detected in the form of a white colony on the surface of the plate culture medium. In the plate culture medium, *E. coli* and EHEC are not multiplied and accordingly are not detected.

The selective medium for EHEC SU 5053 contains the following components per 100 ml distilled water.

| | |
|---|---|
| NaCl | 0.5 g |
| NaH$_2$PO$_4$ | 0.4 g |
| Na$_2$CO$_3$ (anhydrous) | 0.1 g |
| (NH$_4$)$_2$SO$_4$ | 0.2 g |
| MgSO$_4$.7H$_2$O | 0.01 g |
| Raffinose | 0.5 g |
| Sodium thiosulfate (anhydrous) | 0.1 g |
| Agar | 1.5 g |
| Yeast extract | 0.005 g |
| Sodium deoxycholate | 0.02 g |

-continued

| | |
|---|---|
| Sodium linoleate | 0.02 g |
| Neutral red | 0.002 g |
| Van Gieson (Amphotericin B) | 0.0005 g |

The above components except Van Gieson were heated to be dissolved and thereafter were cooled down to about 50° C., and then Van Gieson was added to the resultant composition and mixed to form a plate culture medium (pH of about 7).

When EHEC SU 5053 is inoculated into this plate culture medium and then incubated at about 37° C. for about 48 hours, a large red colony of EHEC SU 5053 is detected. In this plate culture medium, E. coli is detected in the form of a small light pink colony.

The reason why the culture medium flow rate was set at about 5%/hr. is to reproduce a specific state of intestinal tract. The about 5%/hr. is the flow rate at which ingested food is excreted as stools in a day under a healthy intestine. Under a diarrhetic intestine, the flow rate exceeds about 30%/hr.–about 50%/hr. At this fast flow rate, it is hard to carry out an analysis of the interaction of bacteria. For this reason, the culture medium flow rate was set at about 5%/hr. so as to reproduce an initial stage of a diarrhetic state (in other words, a light diarrhetic condition).

Then, 2 ml of Vero toxin detecting culture solution was collected from the above-described culture solution and was centrifuged for 15 minutes at the conditions of about 5° C. and about 4000 rpm. The supernatant was filled in a 2.5 ml injector, and a membrane filter (0.22 μm, Sterile Millex-GV, 0.22 μm filter unit, Low protein binding sterilization (available from Millipore Inc.)) was attached to the tip end of the injector. Further, a test tube sterilized in advance was set with the membrane filter sandwiched between the test tube and the injector. Then, a piston of the injector was pushed to filter and sterilize the supernatant, so as to prepare Vero toxin measuring sample solution (hereinafter it is sometimes simply referred to as "sample solution"). The detection on Vero toxin type I and Vero toxin type II was carried out with the above-described Kit by judging whether the Vero toxin measuring sample solution agglutinated or not.

To be more specific, 25 μl of diluent included in the Kit was put into each of the wells in the 1st, 2nd and 3rd columns of a 96-wells (12 columns×8 rows) microplate included in the Kit. Then, 25 μl of Vero toxin measuring sample solution was added to each of the wells in the 1st row, to prepare twofold diluted sample solution. After the diluent and the Vero toxins measuring sample solution were fully mixed, 25 μl of the mixture was pipetted from each of the wells in the 1st row and in turn was injected into each of the wells in the 2nd row, to prepare fourfold diluted sample solution. The same operation was repeated till the 8th row, to prepare 8-fold diluted sample solution, 16-fold diluted sample solution, 32-fold diluted sample solution, 64-fold diluted sample solution, 128-fold diluted sample solution and 256-fold diluted sample solution (25 μl each), respectively. Similarly, as for control Vero toxins type I and control Vero toxins type II included in the Kit, the 2-fold to 256-fold diluted sample solution were prepared in the same manner as in the above (in the 4th column and 5th column, which are referred to as "measuring control solution" in each of the TABLES). It is noted that as for the 256-fold diluted sample solution in the wells in the 8th row, each of the 128-fold diluted sample solution (25 μl) and the Vero toxin measuring sample solution (25 μl) were fully mixed and thereafter the 256-fold diluted solution of 25 μl was removed from each of the wells.

Then, the sensitization latex VT1 included in the Kit was added to each of the wells in the 1st column (8 wells in total), the sensitization latex VT2 included in the Kit was added to each of the wells in the 2nd column (8 wells in total), and the control latex included in the Kit was added to each of the wells (8 wells in total) in the 3rd column. Similarly, the sensitization latex VT1 and the sensitization latex VT2 were added to the wells in the 4th column and those in the 5th column, respectively. Then, the microplate was shaken with a blender for the intimate mixing and then was allowed to stand overnight at room temperature, to make the judgment. It was confirmed that no control latex in the 3rd column agglutinated, and then those agglutinated by the sensitization latex were defined as positive (+) and those not agglutinated as negative (−). The dilution ratio of the highest multiple of dilution at which the Vero toxin measuring sample solution is agglutinated to cause the Vero toxin type I and the Vero toxin type II to be positive was defined as the agglutination positive maximum dilution ratio and the maximum dilution ratio of the sample solution showing the agglutination positive was defined as an agglutinin titer or the amount of toxins.

Immediately after the above-described Vero toxin detecting culture solution was collected from the culture solution, fosfomycin disodium salt (available from Sigma Chemical Co., Ltd. (USA), hereinafter it is simply referred to as "fosfomycin") was added thereto so that the concentration could become about 250 μg/ml and then was incubated for 24 hours. After incubation for 24 hours (or after 48 hours passed since the inoculation of bacteria), the numbers of bacteria of *E. coli* ATCC 25922, *Clostridium butyricum* FERM P-14285 and EHEC SU 5053 were each measured in the same manner as in the above to detect the Vero toxin type I and the Vero toxin type II. Thereafter, the incubation was carried out for further 48 hours. After incubation for 48 hours (96 hours after the inoculation of bacteria/72 hours after the addition of fosfomycin), the numbers of bacteria of *E. coli* ATCC 25922, *Clostridium butyricum* FERM P-14285 and EHEC SU 5053 were each measured in the same manner as in the above.

The reason why the amount of fosfomycin to be added was set at 250 μg/ml is that when oral administration (a prescribed amount) of the fosfomycin is made, about 200 μg/ml to 600 μg/ml of fosfomycin is contained in the stool (Cf. SATO, Hajime et. al., *Pediatrics Clinical*, 37(9):199–214, 1984). In addition, it is known that under anaerobic conditions, MIC (minimum inhibitory concentration) of the fosfomycin against EHEC SU 5053 is about 12.5 μg/ml and MIC of the fosfomycin against *E. coli* ATCC 25922 is about 50 μg/ml.

The number of bacteria in Example 1 is shown in TABLE 1, and the detection results on the Vero toxins are shown in TABLE 2 (24 hours after the inoculation of bacteria/immediately before the addition of fosfomycin) and in TABLE 3 (48 hours after the inoculation of bacteria/24 hours after the addition of fosfomycin). The summary of the TABLES 1 to 3 is shown in FIG. 1, in which the ordinate at the left side represents the number of bacteria; the ordinate at the right side represents the agglutination positive maximum dilution ratio; and the abscissa represents the culture time.

TABLE 1

The number of bacteria in Example 1 (Unit: log cfu/ml)

| | Immediately after inoculation of bacteria | 24 hrs. after inoculation of bacteria (immediately before addition of fosfomycin) | 48 hrs. after inoculation of bacteria (24 hrs. after addition of fosfomycin) | 96 hrs. after inoculation of bacteria (72 hrs. after addition of fosfomycin) |
|---|---|---|---|---|
| E. coli ATCC 25922 | 6 | 8.4 | 8.3 | 7.6 |
| EHEC SU 5053 | 6 | 7.9 | 6 | 3.4 |
| Clostridium butyricum FERM P-14285 | 6 | 7.9 | 5.2 | 4.2 |

TABLE 2

Detection of Vero toxins in 24 hrs. after the initiation of culture (immediately before the addition of fosfomycin) in Example 1

| | Vero toxin measuring sample solution | | | Measuring control solution (1) | |
|---|---|---|---|---|---|
| Dilution ratio | Vero toxin type I | Vero toxin type II | Control latex | Vero toxin type I | Vero toxin type II |
| 2-fold | − | + | − | + | + |
| 4-fold | − | + | − | + | + |
| 8-fold | − | + | − | + | + |
| 16-fold | − | − | − | + | + |
| 32-fold | − | − | − | + | + |
| 64-fold | − | − | − | − | − |
| 128-fold | − | − | − | − | − |
| 256-fold | − | − | − | − | − |
| Agglutination positive maximum dilution ratio | 2-fold> | 8-fold | 2-fold> | 32-fold | 32-fold |

+: Positive
−: Negative
(1): Prepared from Vero toxins included in the *Escherichia coli* Vero toxin detection Kit available from Denka Seiken Co., Ltd..

TABLE 3

Detection of Vero toxins in 48 hrs. after the initiation of culture (24 hrs. after the addition of fosfomycin) in Example 1

| | Vero toxin measuring sample solution | | | Measuring control solution | |
|---|---|---|---|---|---|
| Dilution ratio | Vero toxin type I | Vero toxin type II | Control latex | Vero toxin type I | Vero toxin type II |
| 2 fold | − | + | − | + | + |
| 4-fold | − | + | − | + | + |
| 8-fold | − | + | − | + | + |

TABLE 3-continued

Detection of Vero toxins in 48 hrs. after the initiation of culture (24 hrs. after the addition of fosfomycin) in Example 1

| | Vero toxin measuring sample solution | | | Measuring control solution | |
|---|---|---|---|---|---|
| Dilution ratio | Vero toxin type I | Vero toxin type II | Control latex | Vero toxin type I | Vero toxin type II |
| 16-fold | − | − | − | + | + |
| 32-fold | − | − | − | + | + |
| 64-fold | − | − | − | − | − |
| 128-fold | − | − | − | − | − |
| 256-fold | − | − | − | − | − |
| Agglutination positive maximum dilution ratio | 2-fold> | 8-fold | 2-fold> | 32-fold | 32-fold |

+: Positive
−: Negative

Example 2

Except that *E. coli* ATCC 25922 containing solution was not added to the above-described culture solution (about 130 ml), the culture, the measurement and the detection were carried out in the same manner as in Example 1. The number of bacteria in Example 2 is shown in TABLE 4, and the detection results on the Vero toxins are shown in TABLE 5 (24 hours after the initiation of culture/immediately before the addition of fosfomycin) and in TABLE 6 (48 hours after the initiation of culture/24 hours after the addition of fosfomycin). The summary of the TABLES 4 to 6 is shown in FIG. 2, in which the ordinate at the left side represents the number of bacteria; the ordinate at the right side represents the agglutination positive maximum dilution ratio; and the abscissa represents the culture time.

TABLE 4

The number of bacteria in Example 2 (Unit: log cfu/ml)

| | Immediately after inoculation of bacteria | 24 hrs. after inoculation of bacteria (immediately before addition of fosfomycin) | 48 hrs. after inoculation of bacteria (24 hrs. after addition of fosfomycin) | 96 hrs. after inoculation of bacteria (72 hrs. after addition of fosfomycin) |
|---|---|---|---|---|
| EHEC SU 5053 | 6 | 8.8 | 7.6 | 7.6 |
| *Clostridium butyricum* FERM P-14285 | 6 | 7.7 | 6.8 | 6.3 |

TABLE 5

Detection of Vero toxins in 24 hrs. after the initiation of culture (immediately before the addition of fosfomyc

TABLE 8

Detection of Vero toxins in 24 hrs. after the initiation of culture (immediately before the addition of fosfomycin) in Example 2

| Dilution ratio | Vero toxin measuring sample solution | | | Measuring control solution | |
| --- | --- | --- | --- | --- | --- |
| | Vero toxin type I | Vero toxin type II | Control latex | Vero toxin type I | Vero toxin type II |
| 2-fold | + | + | − | + | + |
| 4-fold | − | + | − | + | + |
| 8-fold | − | + | − | + | + |
| 16-fold | − | − | − | + | + |
| 32-fold | − | − | − | + | + |
| 64-fold | − | − | − | − | − |
| 128-fold | − | − | − | − | − |
| 256-fold | − | − | − | − | − |
| Agglutination positive maximum dilution ratio | 2-fold | 8-fold | 2-fold> | 32-fold | 32-fold |

+: Positive
−: Negative

TABLE 9

Detection of Vero toxins in 29 hrs. after the initiation of culture (5 hrs. from the addition of fosfomycin) in Compara. Ex. 1

| Dilution ratio | Vero toxin measuring sample solution | | | Measuring control solution | |
| --- | --- | --- | --- | --- | --- |
| | Vero toxin type I | Vero toxin type II | Control latex | Vero toxin type I | Vero toxin type II |
| 2-fold | + | + | − | + | + |
| 4-fold | − | + | − | + | + |
| 8-fold | − | + | − | + | + |
| 16-fold | − | − | − | + | + |
| 32-fold | − | − | − | + | + |
| 64-fold | − | − | − | − | − |
| 128-fold | − | − | − | − | − |
| 256-fold | − | − | − | − | − |
| Agglutination positive maximum dilution ratio | 2-fold | 8-fold | 2-fold> | 32-fold | 32-fold |

+: Positive
−: Negative

TABLE 10

Detection of Vero toxins in 48 hrs. after the initiation of culture (24 hrs. after the addition of fosfomycin) in Compara. Ex. 1

| Dilution ratio | Vero toxin measuring sample solution | | | Measuring control solution | |
| --- | --- | --- | --- | --- | --- |
| | Vero toxin type I | Vero toxin type II | Control latex | Vero toxin type I | Vero toxin type II |
| 2-fold | + | + | − | + | + |
| 4-fold | + | + | − | + | + |
| 8-fold | + | + | − | + | + |
| 16-fold | + | + | − | + | + |
| 32-fold | + | + | − | + | + |
| 64-fold | − | + | − | − | − |
| 128-fold | − | + | − | − | − |
| 256-fold | − | + | − | − | − |
| Agglutination positive maximum dilution ratio | 32-fold | 256-fold | 2-fold> | 32-fold | 32-fold |

+: Positive
−: Negative

Comparative Example 2

Figure 4:
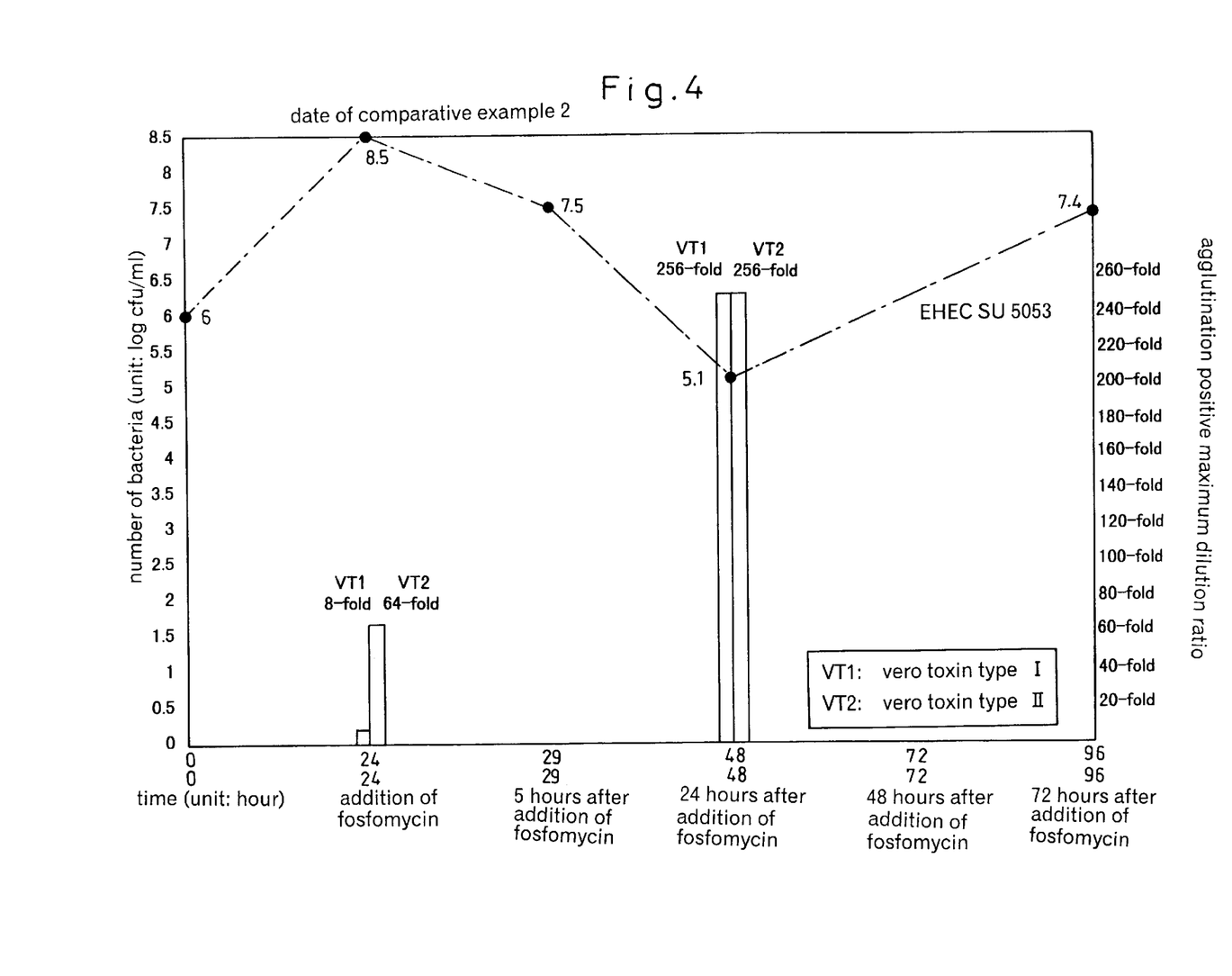
FIG. 4 is a graph summarizing the data of Comparative Example 2.

Except that *Clostridium butyricum* FERM P-14285 was not inoculated in but only EHEC SU 5053 containing solution was inoculated in the culture solution as described above (about 130 ml) to cause the concentration to be about $10^6$ cfu/ml, the culture, the measurement and the detection were carried out in the same manner as in Example 2. The number of bacteria in Comparative Example 2 is shown in TABLE 11, and the detection results on the Vero toxins are shown in TABLE 12 (24 hours after the initiation of culture/ immediately before the addition of fosfomycin) and TABLE 13 (48 hours after the initiation of culture/24 hours after the addition of fosfomycin). The summary of the TABLES 11 to 13 is shown in FIG. 4, in which the ordinate at the left side represents the number of bacteria; the ordinate at the right side represents the agglutination positive maximum dilution ratio; and the abscissa represents the culture time.

TABLE 11

The number of bacteria in Compara. Ex. 2 (Unit: log cfu/ml)

| | Immediately after inoculation of bacteria | 24 hrs. after inoculation of bacteria (immediately before addition of fosfomycin) | 29 hrs. after inoculation of bacteria (5 hrs. after addition of fosfomycin) | 48 hrs. after inoculation of bacteria (24 hrs. after addition of fosfomycin) | 96 hrs. after inoculation of bacteria (72 hrs. after addition of fosfomycin) |
| --- | --- | --- | --- | --- | --- |
| EHEC SU 5053 | 6 | 8.5 | 7.5 | 5.1 | 7.4 |

TABLE 12

Detection of Vero toxins in 24 hrs. after the initiation of culture
(immediately before the addition of fosfomycin) in Compara. Ex. 2

| Dilution ratio | Vero toxin measuring sample solution | | | Measuring control solution | |
| --- | --- | --- | --- | --- | --- |
| | Vero toxin type I | Vero toxin type II | Control latex | Vero toxin type I | Vero toxin type II |
| 2-fold | + | + | − | + | + |
| 4-fold | + | + | − | + | + |
| 8-fold | + | + | − | + | + |
| 16-fold | − | + | − | + | + |
| 32-fold | − | + | − | + | + |
| 64-fold | − | + | − | − | − |
| 128-fold | − | − | − | − | − |
| 256-fold | − | − | − | − | − |
| Agglutination positive maximum dilution ratio | 8-fold | 64-fold | 2-fold> | 32-fold | 32-fold |

+: Positive
−: Negative

TABLE 13

Detection of Vero toxins in 48 hrs. after the initiation of culture
(24 hrs. after the addition of fosfomycin) in Compara. Ex. 2

| Dilution ratio | Vero toxin measuring sample solution | | | Measuring control solution | |
| --- | --- | --- | --- | --- | --- |
| | Vero toxin type I | Vero toxin type II | Control latex | Vero toxin type I | Vero toxin type II |
| 2-fold | + | + | − | + | + |
| 4-fold | + | + | − | + | + |
| 8-fold | + | + | − | + | + |
| 16-fold | + | + | − | + | + |
| 32-fold | + | + | − | + | + |
| 64-fold | + | + | − | − | − |
| 128-fold | + | + | − | − | − |
| 256-fold | + | + | − | − | − |
| Agglutination positive maximum dilution ratio | 256-fold | 256-fold | 2-fold> | 32-fold | 32-fold |

+: Positive
−: Negative

Figure 1:
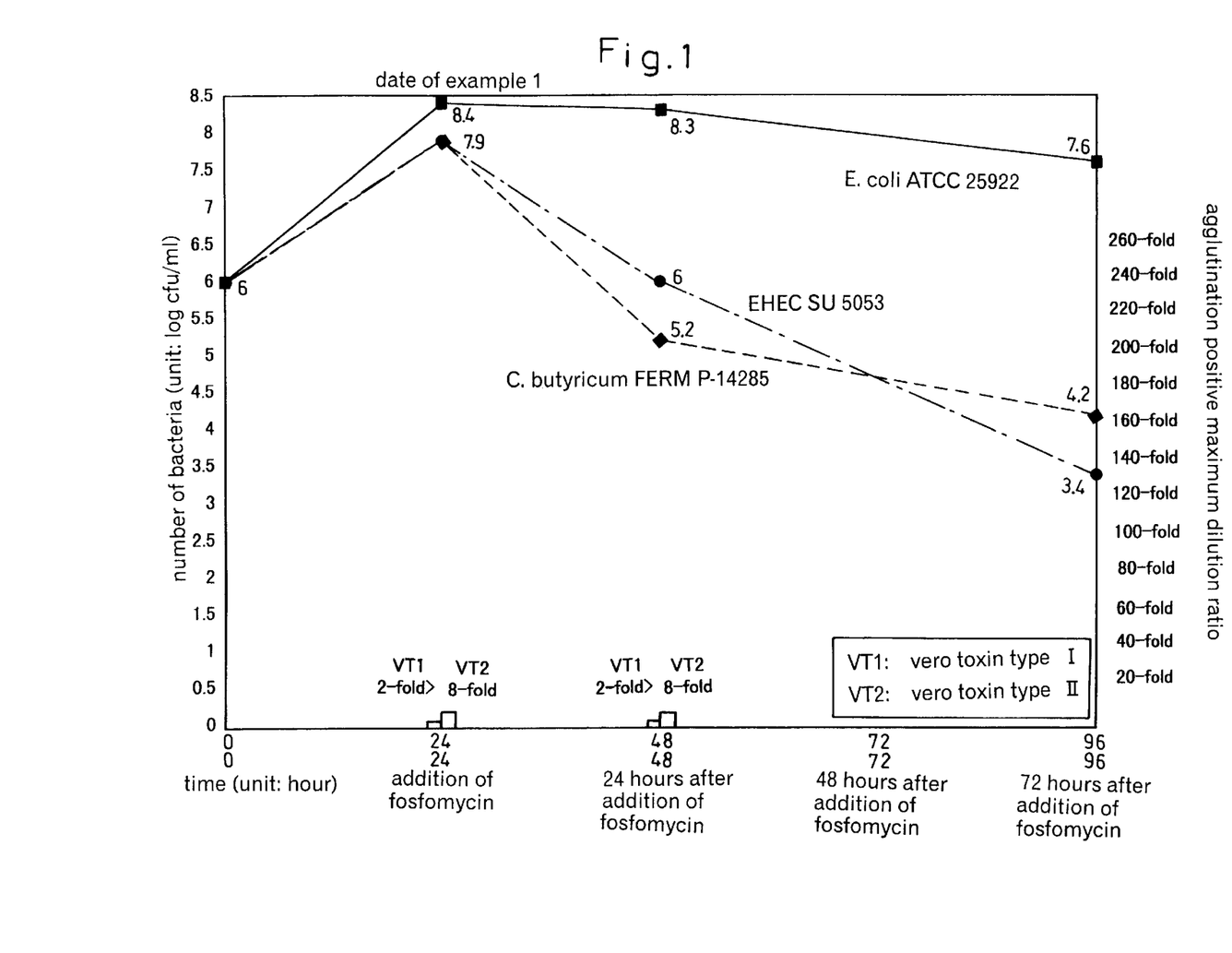
FIG. 1 is a graph summarizing the data of Example 1.
Figure 3:
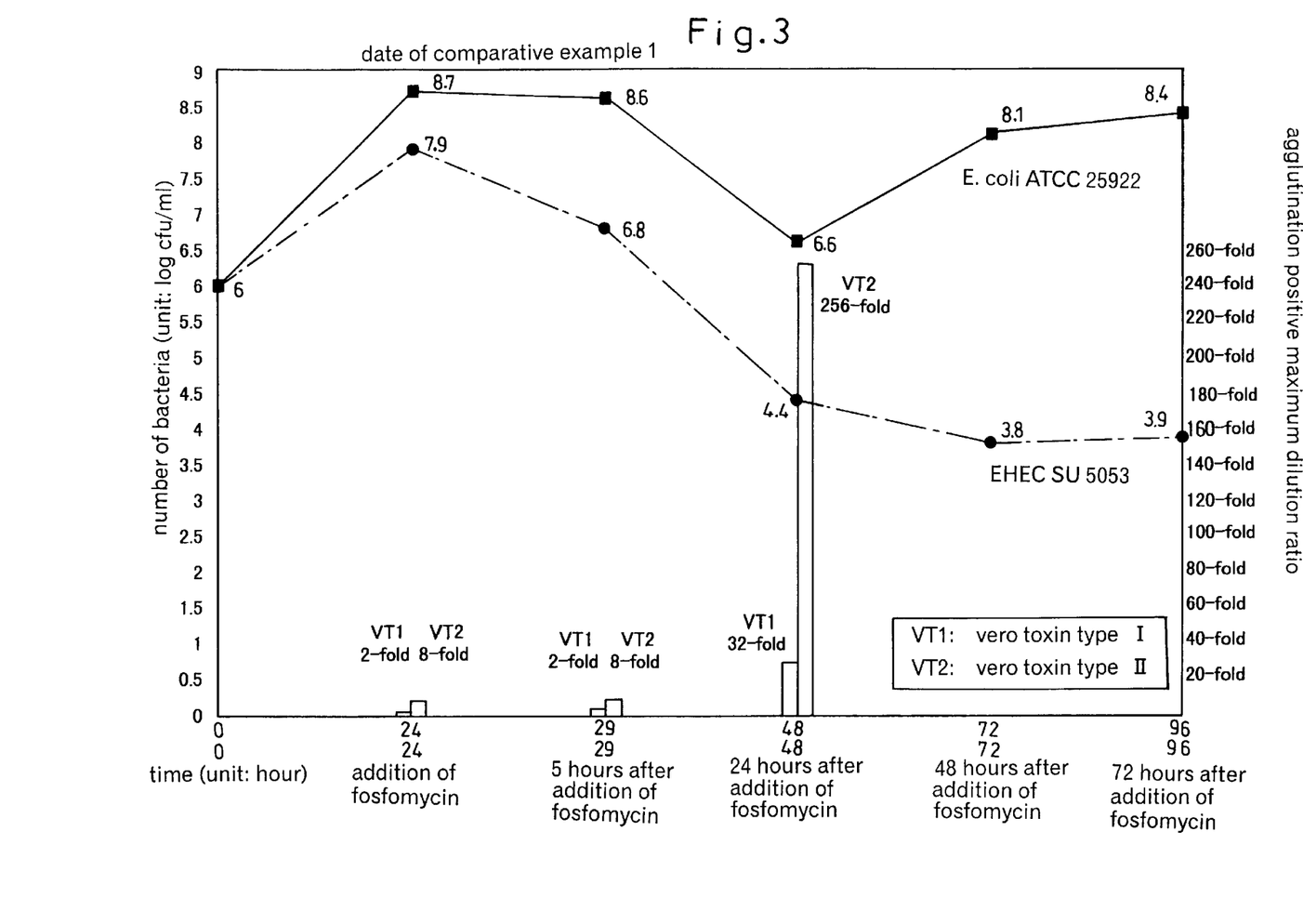
FIG. 3 is a graph summarizing the data of Comparative Example 1.

It is understood from Example 1 and Comparative Example 1 that the production of Vero toxins after 24 hours from the addition of fosfomycin was inhibited more strongly in the culture solution in which *Clostridium butyricum* FERM P-14285 was inoculated (Example 1, TABLES 1 to 3 and FIG. 1) than in the culture solution in which no *Clostridium butyricum* FERM P-14285 was inoculated (Comparative Example 1, TABLES 7–10 and FIG. 3). It is also understood from the comparison between the number of bacteria of EHEC SU 5053 in 24 hours after the inoculation of bacteria and that in 96 hours after the inoculation of bacteria that in either case, the number of bacteria of EHEC SU 5053 is reduced to about $\frac{1}{10,000}$th, so that *Clostridium butyricum* FERM P-14285 exerts almost no harmful influence on the sterilizing action of fosfomycin against EHEC SU 5053. Thus, the production of Vero toxins is inhibited by the method of the invention, so that the enteropathogenic *Escherichia coli* EHEC is sterilized very safely in an area contaminated by the enteropathogenic *Escherichia coli* EHEC (e.g. the intestinal tract).

Figure 2:
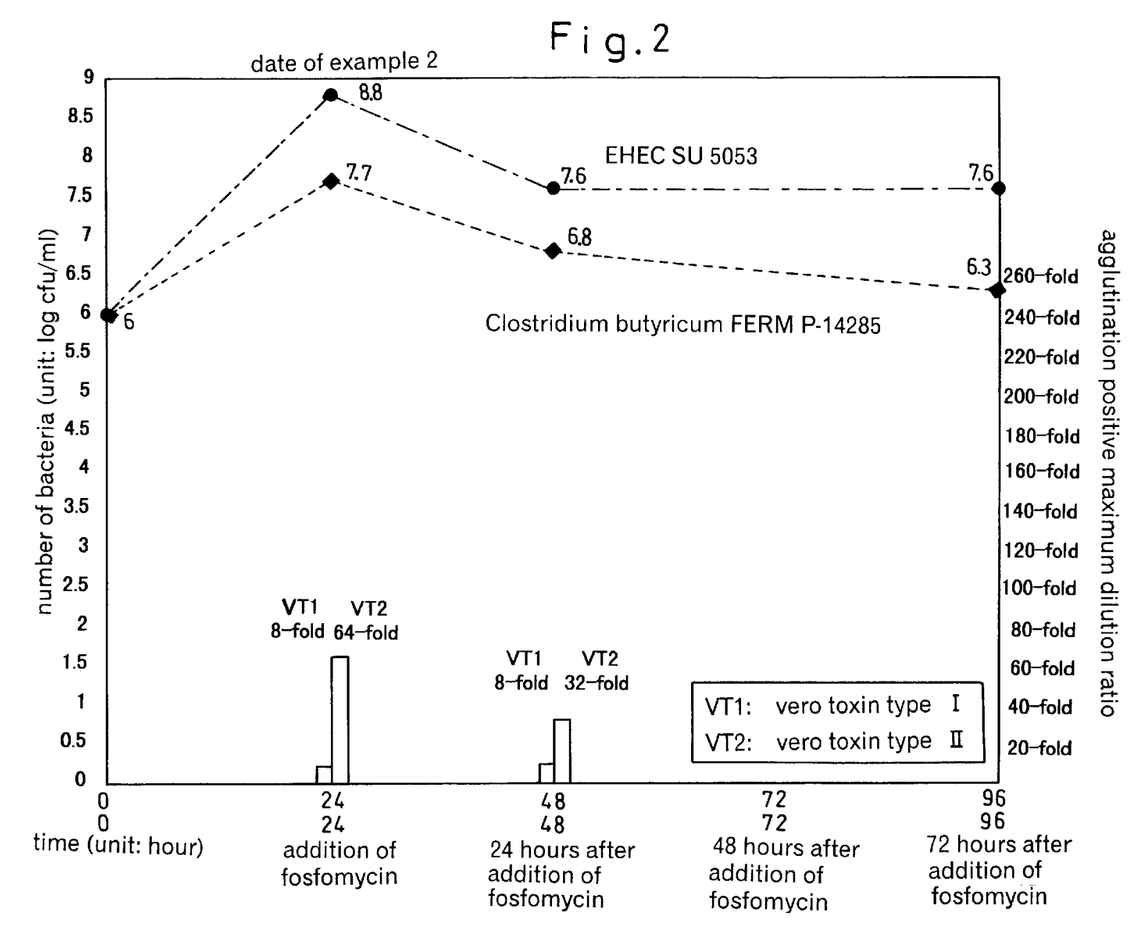
FIG. 2 is a graph summarizing the data of Example 2.

It is understood from Example 2 and Comparative Example 2 that the production of Vero toxins in 24 hours from the addition of fosfomycin was apparently inhibited in the culture solution in which *Clostridium butyricum* FERM P-14285 was inoculated (Example 2, TABLES 4 to 6 and FIG. 2), as compared with in the culture solution in which no *Clostridium butyricum* FERM P-14285 was inoculated (Comparative Example 2, TABLES 11–13 and FIG. 4), as in the case of the above.

Also, it is seen from comparison between Example 1 (TABLES 1 to 3, FIG. 1) and Example 2 (TABLES 4 to 6, FIG. 2) that when not only *Clostridium butyricum* FERM P-14285 but also *E. coli* ATCC 25922 were inoculated in the culture solution in the presence of fosfomycin, EHEC SU 5053 was sterilized more strongly, while also the production of Vero toxins was inhibited further significantly. It is thus understood from this that the production of Vero toxins is inhibited by *Clostridium butyricum*FERM P-14285 being used in combination with fosfomycin, and sequentially EHEC SU 5053 is sterilized, while also, the production of Vero toxins is inhibited further significantly by the interaction between such combination and *E. coli* ATCC 25922, and sequentially the EHEC SU 5053 is sterilized further significantly.

Example 3

Described in this Example are butyric-acid bacteria containing pharmaceuticals used in combination with antibiotics to inhibit the production of toxins from the enteropathogenic *Escherichia coli*.

*Clostridium butyricum* FERM P-14285 was inoculated in known culture solution which was sterilized with an autoclave at about 121° C. for about 15 minutes and then incubated at about 37° C. for about 24 hours, to prepare culture solution A.

On the other hand, another known liquid medium was applied to a flask and was sterilized in the same manner. Thereafter, the culture solution A was added to the liquid medium and then was incubated at about 37° C. for about 24 hours to prepare culture solution B. On the other hand, the culture solution B was added into a culture tank in which known liquid medium was applied and sterilized, and then was incubated at about 37° C. for about 24 hours to prepare culture solution C. Then, the culture solution C was centrifuged for about 2 hours at 12,000 rpm to collect the deposits. Then, the deposits and lactose were added to tap water, and the resultant was freeze-dry lyophilized to prepare bacteria powder of butyric-acid bacteria. Then, the bacteria powder of butyric-acid bacteria and dried potato starch were mixed and sifted through a 60 mesh sieve, to prepare butyric-acid bacteria containing pharmaceuticals.

The butyric-acid bacteria containing pharmaceuticals thus prepared, containing *Clostridium butyricum* FERM P-14285, enable the production of Vero toxins from enteropathogenic *Escherichia coli* EHEC (O157) to be inhibited and also enable the Vero toxins to be safely sterilized by being added together with an antibiotic such as fosfomycin to an area contaminated by the Vero toxins from the enteropathogenic *Escherichia coli* EHEC (O157).

Thus, the present invention can provide the method for inhibiting the production of toxins (Vero toxins, in particular) of enteropathogenic *Escherichia coli* significantly, the method for safely sterilizing the enteropathogenic *Escherichia coli*, and butyric-acid bacteria and butyric-acid bacteria containing pharmaceuticals to be used for the method.

What is claimed is:

1. A method for treating a human infected with enteropathogenic *Escherichia coli* which produces toxins comprising administering to the human a *Clostridium butyricum* and fosfomycin or a metallic salt thereof in amounts effective to inhibit the enteropathogenic *Escherichia coli* from producing said toxins.

2. The method according to claim 1, which further comprises administering to said human, human intestine indigenous *Escherichia coli*.

3. The method according to claim 1, wherein said *Clostridium butyricum* butyric-acid is *Clostridium butyricum* FERM BP-6393.

4. The method according to claim 1, wherein said enteropathogenic *Escherichia coli* is enterohemorrhagic *Escherichia coli* (EHEC).

5. The method according to claim 4, wherein said enterohemorrhagic *Escherichia coli* (EHEC) is EHEC SU 5053 (O157).

6. The method according to claim 1, wherein said toxins are Vero toxins.

7. A pharmaceutical composition comprising a *Clostridium butyricum* and fosfomycin or a metallic salt thereof in amounts effective to inhibit production of toxins from enteropathogenic *Escherichia coli*, in combination with a pharmaceutically acceptable carrier.

8. The pharmaceutical composition according to claim 7, wherein said *Clostridium butyricum* is *Clostridium butyricum* FERM BP-6393.

9. The pharmaceutical composition according to claim 8, which further comprises an antibiotic to inhibit the production of toxins from enteropathogenic *Escherichia coli*.

10. The pharmaceutical composition according to claim 8, which further comprises a human intestine indigenous *Escherichia coli*.

* * * * *